(12) United States Patent
Evins et al.

(10) Patent No.: US 12,396,674 B2
(45) Date of Patent: Aug. 26, 2025

(54) SYSTEM AND METHOD FOR DETECTING ACUTE BRAIN FUNCTION IMPAIRMENT

(71) Applicant: The General Hospital Corporation, Boston, MA (US)

(72) Inventors: A. Eden Evins, Concord, MA (US); Jodi M. Gilman, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 815 days.

(21) Appl. No.: 16/323,043

(22) PCT Filed: Aug. 4, 2017

(86) PCT No.: PCT/US2017/045541
§ 371 (c)(1),
(2) Date: Feb. 4, 2019

(87) PCT Pub. No.: WO2018/027151
PCT Pub. Date: Feb. 8, 2018

(65) Prior Publication Data
US 2019/0167177 A1 Jun. 6, 2019

Related U.S. Application Data

(60) Provisional application No. 62/370,966, filed on Aug. 4, 2016, provisional application No. 62/393,405, filed on Sep. 12, 2016.

(51) Int. Cl.
A61B 5/00 (2006.01)
A61B 5/372 (2021.01)
G06N 20/00 (2019.01)

(52) U.S. Cl.
CPC .......... *A61B 5/4064* (2013.01); *A61B 5/0075* (2013.01); *A61B 5/372* (2021.01); *A61B 5/7267* (2013.01); *A61B 5/6803* (2013.01); *G06N 20/00* (2019.01)

(58) Field of Classification Search
None
See application file for complete search history.

(56) References Cited

U.S. PATENT DOCUMENTS

| 8,237,118 | B2 | 8/2012 | Prox | |
|---|---|---|---|---|
| 10,136,830 | B2 | 11/2018 | Geva et al. | |
| 2003/0013981 | A1* | 1/2003 | Gevins | A61B 5/377 600/544 |

(Continued)

FOREIGN PATENT DOCUMENTS

WO WO-2013011515 A1 * 1/2013 ............. A61B 5/048

OTHER PUBLICATIONS

Li et al., "Functional connectivity changes between parietal and prefrontal cortices in primary insomnia patients: evidence from resting-state fMRI", European Journal of Medical Research, vol. 19, Issue 32, pp. 1-7, 2014. (Year: 2014).*

(Continued)

*Primary Examiner* — Katherine L Fernandez
(74) *Attorney, Agent, or Firm* — QUARLES & BRADY LLP

(57) ABSTRACT

A system and method is provided for acquiring data from a brain of a subject and analyzing the data to generate an indication of a level of acute impairment of the subject.

13 Claims, 15 Drawing Sheets

(56) References Cited

U.S. PATENT DOCUMENTS

| | | | |
|---|---|---|---|
| 2011/0245708 A1* | 10/2011 | Finkel | A61B 5/4824 600/544 |
| 2013/0035579 A1* | 2/2013 | Le | A61B 5/316 600/383 |
| 2014/0023999 A1 | 1/2014 | Greder | |
| 2014/0288454 A1 | 9/2014 | Paz | |
| 2014/0308687 A1 | 10/2014 | Keller | |
| 2015/0088024 A1 | 3/2015 | Sackellares | |
| 2015/0148700 A1* | 5/2015 | Mhuircheartaigh | A61B 5/6803 604/66 |
| 2016/0022168 A1* | 1/2016 | Luczak | A61N 1/0531 600/544 |
| 2016/0038049 A1* | 2/2016 | Geva | A61B 5/7267 600/544 |
| 2018/0184964 A1* | 7/2018 | Simon | A61B 5/002 |
| 2020/0038653 A1* | 2/2020 | Sitaram | A61B 5/055 |

OTHER PUBLICATIONS

"Intoxication Definition and Meaning", Merriam-Webster Dictionary, https://www.merriam-webster.com/dictionary/intoxication. Accessed Jun. 3, 2024.*

"Intoxication", HRB National Drugs Library, https://www.drugsandalcohol.ie/glossary/search?search_string=intoxication&search_fields=title&order_by=none&submit=Search. Accessed Jun. 3, 2024.*

"Scopolamine", Wikipedia, https://en.wikipedia.org/wiki/Scopolamine#:~: text=Scopolamine%20acts%20as%20a%20nonspecific,the%20M1%20muscarinic%20receptor. Accessed Jun. 3, 2024.*

Compton, R. P. Marijuana-impaired driving-a report to congress. No. DOT HS 812 440. United States. National Highway Traffic Safety Administration, 2017.

European Patent Office, Extended European Search Report for application 17837775.0. Mailed on Nov. 20, 2019.

International Searching Authority, International Search Report and Written Opinion for application PCT/US2017/045541. Mailed on Oct. 18, 2017.

Ní Mhuircheartaigh, Róisín, et al. "Slow-wave activity saturation and thalamocortical isolation during propofol anesthesia in humans." Science translational medicine 5.208 (2013): 208ra148-208ra148.

Reches, Amit, et al. "Brain Network Activation (BNA) reveals scopolamine-induced impairment of visual working memory." Journal of Molecular Neuroscience 54 (2014): 59-70.

Stern, Yaki, Amit Reches, and Amir B. Geva. "Brain network activation analysis utilizing spatiotemporal features for event related potentials classification." Frontiers in computational neuroscience 10 (2016): 137.

* cited by examiner

SYSTEM AND METHOD FOR DETECTING ACUTE BRAIN FUNCTION IMPAIRMENT

CROSS REFERENCE TO RELATED APPLICATIONS

This application is a U.S. National Stage of PCT Application No. PCT/US2017/045541 filed on Aug. 4, 2017 which is based on and claims the benefit of U.S. Provisional Application Ser. No. 62/370,966 filed on Aug. 4, 2016, and entitled "Using Portable Imaging Technology to Determine Intoxication in Humans," and U.S. Provisional Application Ser. No. 62/393,405 filed on Sep. 12, 2016, and entitled "Using Portable Imaging Technology to Determine Intoxication in Humans," and each of which are incorporated herein by reference in its entirety.

STATEMENT REGARDING FEDERALLY SPONSORED RESEARCH

This invention was made with government support under K24 DA030443 and K01 034093 awarded by the National Institutes of Health. The government has certain rights in the invention.

BACKGROUND

The present disclosure relates to systems and methods for detecting acute impairment. More particularly, the present disclosure provides systems and methods to improve the portability and reliability of determining impairment.

Impairment can significantly affect activities including, but not limited to, driving, operating machinery, and performing cognitive tasks and can stem from a variety of causes, from lack of sleep to consumption of intoxicants. That is, intoxication can contribute to or cause impairment, and can result from an individual metabolizing a variety of things, including alcohol and drugs. Impairment due to intoxication is a factor in approximately 25% of motor vehicle accidents. As one example, marijuana (MJ) can contribute to the prevalence of driving while intoxicated. After alcohol, MJ is the most frequently detected drug in drivers involved in car accidents.

The prevalence of detectable Δ9-tetrahydrocannabinol (THC) in body fluids of those detained for DUI increased by 48%, to 27% of drivers, from 2007 to 2014. With marijuana (MJ) legalization across the United States and potency of MJ products at historic highs, driving under the influence of MJ is an increasingly important public health issue. In double-blind, placebo-controlled laboratory studies, THC causes acute, dose-dependent impairment in performance on memory, divided and sustained attention, reaction time, visual tracking and motor function tasks. These are cognitive and motor skills that subserve critical aspects of driving performance. THC acutely impairs driving in simulator and on-road driving tests. In real-world settings, those who test positive for THC or its metabolites in body fluids have been determined to double the risk of car crashes compared with those without. Prevalence of MJ-drugged driving is projected to continue increase with widening societal acceptance of MJ use worldwide. The ability to detect alcohol intoxication with a road-side breathalyzer has been shown to reduce alcohol-involved traffic crashes. However, detecting overall impairment or impairment caused by substances other than alcohol can be difficult. For example, the breathalyzer does not detect impairment, but instead correlates to blood alcohol levels. As such, it does not indicate individual impairment and provide information on other substances besides alcohol that can cause impairment.

Therefore, it would be desirable to have a system and method for detecting acute brain function impairment that has broader capabilities than mere blood alcohol level, while also being simple and reliable.

SUMMARY

The present disclosure overcomes the aforementioned drawbacks by providing a system and method for detecting acute brain function impairment that may be portable and accurate.

In accordance with the present disclosure, a system is provided for determining an acute brain function impairment of a subject. The system includes a sensor system configured to acquire signals indicative of a function of a brain of the subject and a processor configured to receive the signals from the sensor. The processor is configured to analyze the signals to determine an amount of functional connectivity between portions of the brain of the subject from the signals and compare the amount of functional connectivity between portions of the brain of the subject to a reference amount of functional connectivity. The processor is further configured to determine an acute impairment of the subject based on the comparison of the amount of functional connectivity between portions of the brain of the subject to the reference amount of functional connectivity and generate a report indicating the acute impairment of the subject.

In accordance with another aspect of the disclosure, a method is provided for detecting acute impairment that includes acquiring, with a sensor, signals from a subject indicative of brain functionality of the subject and processing, using a computer processor, the signals to determine functional connectivity of the brain of the subject. The method also includes determining, using the computer processor, whether the functional connectivity of the brain of the subject is indicative of an impairment of the subject and generating a report indicating a level of acute impairment of the subject from the determining of step.

In accordance with yet another aspect of the disclosure, a portable system is provided for detecting acute impairment of a subject. The system includes a detection system that includes at least one sensor configured for placement on a head of the subject to acquire data indicating functionality of a brain of the subject. The system also includes a processor configured to receive the data from the at least one sensor and a display screen in communication with the processor and configured to display at least an indication of an acute impairment state of the subject. The processor is configured to analyze the data and output an indication of the acute impairment state of the subject to the display.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
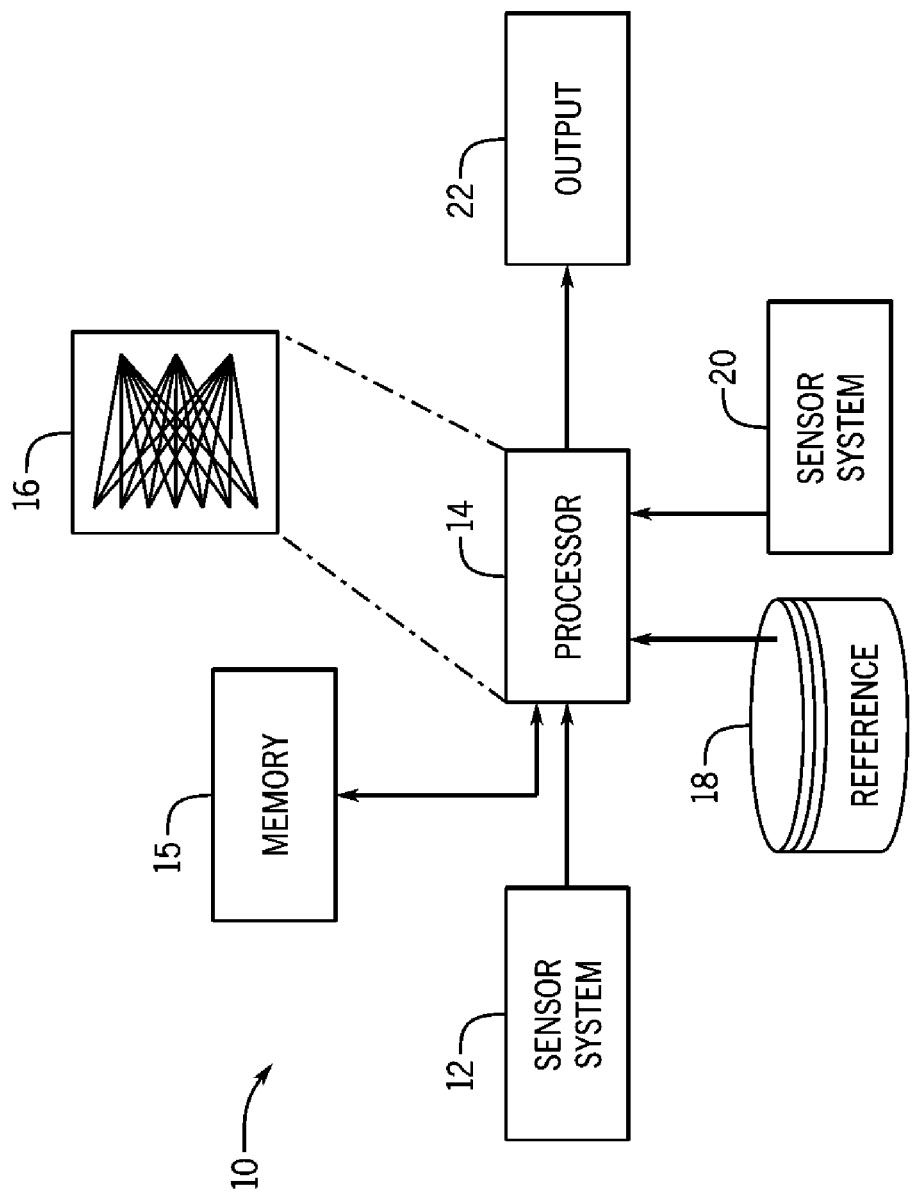
FIG. 1 is a block diagram of a system for assessing acute brain function impairment of an individual in accordance with the present disclosure.

As will be described, systems and methods for detecting and assessing acute brain function impairment are provided. As will be described, acute brain function impairment refers to physical and/or mental performance deficiencies caused by physiological processing, including but not limited to metabolism, of substances, such as drugs and alcohol, typically through the consumption, inhalation, injection, or other intake of the substance. Such an ability to detect and assess acute brain function impairment find particular application in a variety of settings including, as a non-limiting example, by law enforcement and employer, governmental, or sports testing. The detection and assessment of acute brain function impairment may be used with any of a variety of applications that require determining impairment of an individual at a specified time.

Assessing of acute brain function impairment is distinguished from, for example, traditional mechanisms for law enforcement assessment of intoxication through consumption of alcohol or employer/governmental "drug testing." Specifically, law enforcement assessment of intoxication due to alcohol consumption has traditionally relied upon determinations of blood alcohol content (BAC), either through analysis of breath or blood. That is, BAC indicates the amount of alcohol present in the body, but does not indicate the actual level of intoxication of the individual at the time of testing because, as is widely understood, the intoxicating effects of alcohol can vary widely based on individual factors, including weight and tolerance, to name but a few. Thus, though a law enforcement officer may be able to assess that an individual has a particular amount of alcohol present in his or her body, the officer cannot speak to the actual level of physical or mental impairment of the individual being experienced by the individual based on the BAC. Instead, complicated, yet highly subjective, field sobriety tests have been created as a means to assess the actual level of physical or mental impairment of the individual, which are typically used before BAC tests are administered. As a direct reflection of the subject nature of assessing sobriety (i.e., actual level of physical or mental impairment of the individual), laws have been written that rely on a surrogate for intoxication, BAC, rather than the level of intoxication, which is the true target of the laws.

Drug testing also suffers from an inability to assess actual level of physical or mental impairment of the individual caused by drug consumption. In the context of law enforcement, the only field usable resource is the highly-subjective field sobriety test. MJ impairment can be associated with rapid heart rate, hallucinations, mental confusion, panic attacks, slowed or slurred speech, visual impairment, and extreme paranoia or other noticeable cognitive or motor function features. For law enforcement and employers, drug tests can be administered, but they lack any acute nature because such drug tests are look back over a large time range, deliver results that are not contemporaneous with sample collection, and the like. Such drug tests likewise suffer from any ability to indicate actual level of physical or mental impairment of the individual when under the influence of the drug. Like alcohol, the relationship between drug exposure, including frequent versus infrequent use, reflected in measurement of drugs and their metabolites or other biomarkers in the blood, urine, hair, or other samples, and cognitive or motoric impairment may vary dramatically from one individual to another.

Thus, it is extremely difficult to assess acute brain function impairment via traditional methods. As one example, marijuana does not have a specific and quantifiable test to determine whether an individual is acutely intoxicated. The pharmacokinetics of MJ are very different to those of alcohol. While alcohol is metabolized by the liver during the period of intoxication, such that by the time the person is no longer intoxicated, alcohol metabolites have been cleared from the body, the primary intoxicating component of MJ, THC, is rapidly cleared from the bloodstream, on average within 13 minutes of use, while intoxication and resulting impairment can last for hours due to sequestration in the brain. Thus, tests for intoxication that measure THC concentration in body fluids yield many false negative results. THC metabolites, on the other hand, remain in the bloodstream for weeks after last use, long after the period of intoxication is over. Thus, tests for intoxication using THC metabolites in body fluids yield many false positive results for impairment. The pharmacokinetics of MJ make it nearly impossible to identify impairment due to MJ intoxication with a biochemical measurement of THC or THC metabolite concentration in the breath or body fluids. Because of these pharmacokinetic properties, there is not a reliable quantitative test for acute MJ intoxication based on detection of the primary intoxicating component, THC, or its metabolites in body fluids or breath.

Without a quantitative, biologically-based test for impairment due to MJ intoxication, the gold standard for detection of MJ-associated impairment is the field sobriety test. Though trained drug recognition experts report up to 92% accuracy in determination of intoxication with a specific drug type in field tests, their testimony is often successfully challenged in court.

The growing prevalence of states legalizing marijuana for medical and/or recreational use has increased the need for field intoxication analysis. In addition to a raise in acceptance, the THC levels in marijuana are also increasing. For example, from 1995 to 2012, the concentration of THC in marijuana has increased by 226% according to some studies. Prevalence of driving under the influence of MJ is projected to continue increase with widening societal acceptance of MJ use worldwide. This has raised alarm among law enforcement personnel at all levels. Furthermore, MJ is but one example of a common intoxicant that can induce level of physical or mental impairment of the individual. Accordingly, systems and methods are needed to objectively detect and assess acute brain function impairment for a variety of intoxicants, including, but not limited to, alcohol and THC.

As will be described, the present disclosure provides systems and methods to acquire signals from an individual's brain that correlate with brain function and analyze these signals to determine and report on acute brain function impairment of the individual. As will be described, these signals may be acquired using a variety of technologies including, but not limited to, functional near-infrared spectroscopy (fNIRS) and electroencephalograms (EEG). Such systems for acquiring signals form the brain that correlate to a biological measurement indicative of impairment may be implemented according to the present disclosure.

In one non-limiting configuration, the system may be realized as including a headset designed to be coupled to an individual's head, and in some instances, to the individual's forehead. The headset may include a plurality of sensors, which may include emitters and detectors, that may be used to collect data. The collected data may be analyzed to determine biological measurements that can indicate an impairment state of the individual. More specifically, the collected data may be analyzed relative to reference data to determine and generate a report providing a quantitative indication of an acute brain function impairment of the individual. That is, an amount of functional brain connectivity may be determined from the collected data and compared to a reference amount of brain connectivity and a determination of acute brain function impairment be made upon determining an increased amount of brain connectivity relative to the reference amount of connectivity.

As will be described, functional connectivity can be understood through the statistical association or dependency among two or more anatomically distinct time-series of data. Measures of connectivity are agnostic regarding causality or direction of connections; however they are useful to discover patterns (which regions are coupled), and compare patterns, especially between conditions.

Referring to FIG. 1, system for detecting and assessing acute brain function impairment 10 includes a sensor system 12 that acquires data from a subject and provides data to a processor 14. The processor 14 can be configured to access a memory 15 that may store, in addition to other information, a verity of software. For example, the processor 14 may be configured, in some non-limiting examples, to implement a machine learning algorithm, such a random forest classifier or a neural network 16. In this regard, the processor 14, as will be described may be configured to assess data acquired by the sensor system 12 against, for example, a reference set of data 18, which may reside in a database 18 or be acquired by additional sensors 20. The database 18 may reside in the memory 15 or separately, including in the cloud. The processor 14 is configured to generate a report indicating and/or quantifying the assessed acute brain function impairment of the individual, which is then communicated via an output 22, which may be a display or other mechanism for communication, such as a speaker or visual cue.

Figure 2C:
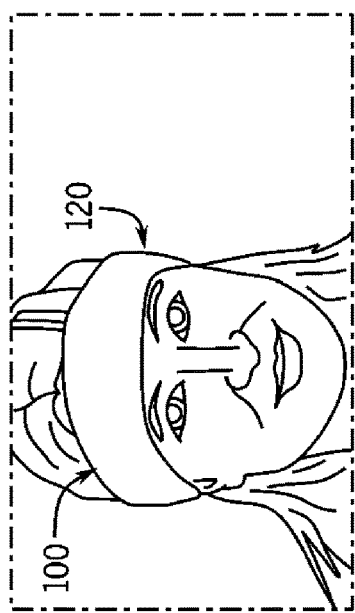
FIG. 2C is a perspective view of a sensor headband in accordance with the present disclosure being worn by an individual undergoing acute brain function impairment assessment.
Figure 2D:
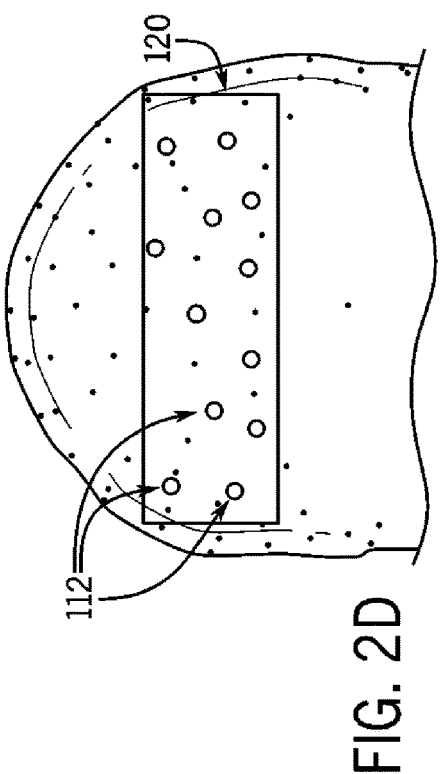
FIG. 2D is a sensor map created using the sensor headband of FIG. 2C
Figure 2A:
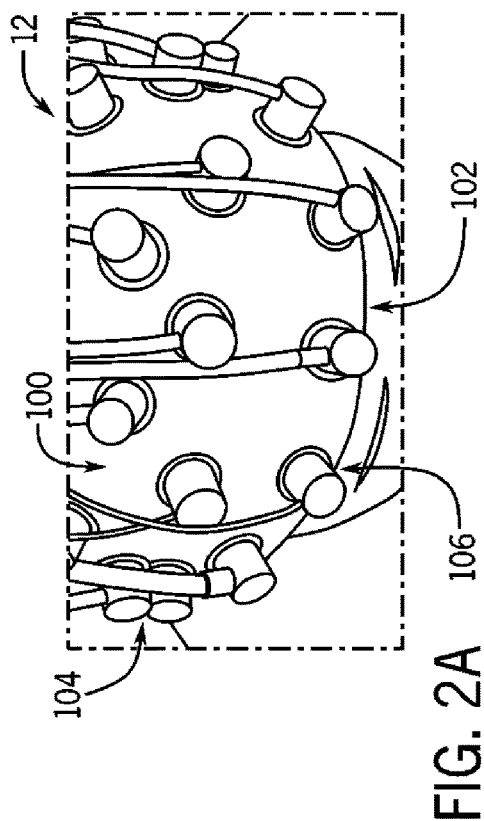
FIG. 2A is a perspective view of a sensor cap in accordance with the present disclosure being worn by an individual undergoing acute brain function impairment assessment.

FIG. 2A is a perspective view of one configuration of the sensor system 12. Specifically, the sensor system 12 includes a substrate 100 that is shaped as a cap 102 that is designed to fit about a subject's head 104. Mounted to the substrate 100 are a plurality of sensors 106. As will be described, each of the sensors 106 are configured to acquire signals from the subject that are indicative of or correlated to a function of the brain of the subject. In some configurations, the sensors 106 may be removeably connected to the substrate 100. This may facilitate the replacement of the sensors as needed and or washing or replacement of the substrate, such that the substrate may be disposable.

Figure 2B:
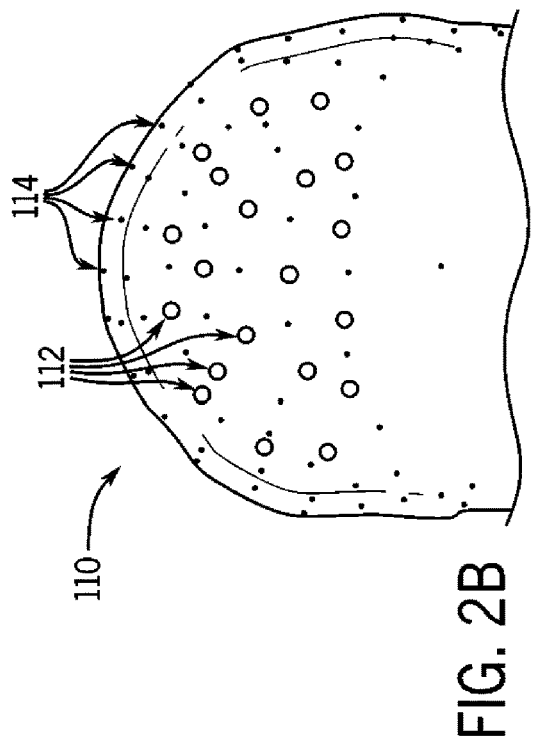
FIG. 2B is a sensor map created using the sensor cap of FIG. 2A.

For example, FIG. 2B provides a map 110 of the input/output characteristics of the sensor system 12 of FIG. 2A when the sensors 106 of FIG. 2A are implemented using near infrared spectroscopy (NIRS) or functional NIRS (fNIRS). fNIRS is a non-invasive technique that uses light absorption properties of hemoglobin to measure oxygenated hemoglobin (Hb) concentrations that arise from cerebral blood flow associated with brain activity. fNIRS detects a local hemodynamic response signal (concentration of oxygenated Hb relative to deoxygenated Hb) analogous to the blood oxygen level dependent response detected by fMRI. fNIRS devices can be implemented in wireless, portable systems that can be quickly fixed to the forehead in field settings.

When the sensors 106 are NIRS or fNIRS sensors, an emission and detection protocol is utilized. As illustrated in FIG. 2B, for each sensor 106, at least one emission signal 112 is generated and one detection signal 114 is received. As illustrated in FIG. 2B, the sensors 106 may form an array of emission signals 112 and detection signals 114. In some configurations, the emission signals 112 and the detection signals 114 may be managed by a transceiver that forms each sensor 106. Alternatively, each sensor 106 may be formed from individual transmitters and detectors. Thus, as used herein, reference to emitters and detectors may refer to discrete components or may refer to a combined transceiver.

Regardless of the particular mechanism for acquiring feedback from an individual, as illustrated in FIGS. 2A and 2B, the array may cover a significant portion of a subject's head. In some configurations, the footprint of the sensing array may be limited to a select array of channels. For example, the above described systems and methods may be implemented using an fNIRS array of 20 channels that is arranged over the forehead of a user. As will be further described, the channels may be designed to detect activity in the prefrontal cortex, and may reliably detect abnormally high prefrontal cortical brain activation, or abnormally high connectivity between brain regions, caused by acute brain function impairment at the individual level. In some situations, it may be beneficial to use fewer channels, which can reduce the footprint of the detection system 10. Further, it may be beneficial to select specific channels, as discussed below. For example, referring to FIG. 2C, the substrate 100 may be formed into a headband 120. In this case, as illustrated in FIG. 2D, the emission signals 112 may be limited to an area corresponding to the headband 120, such that the array covers only a small portion of an subject's head.

Figure 3:
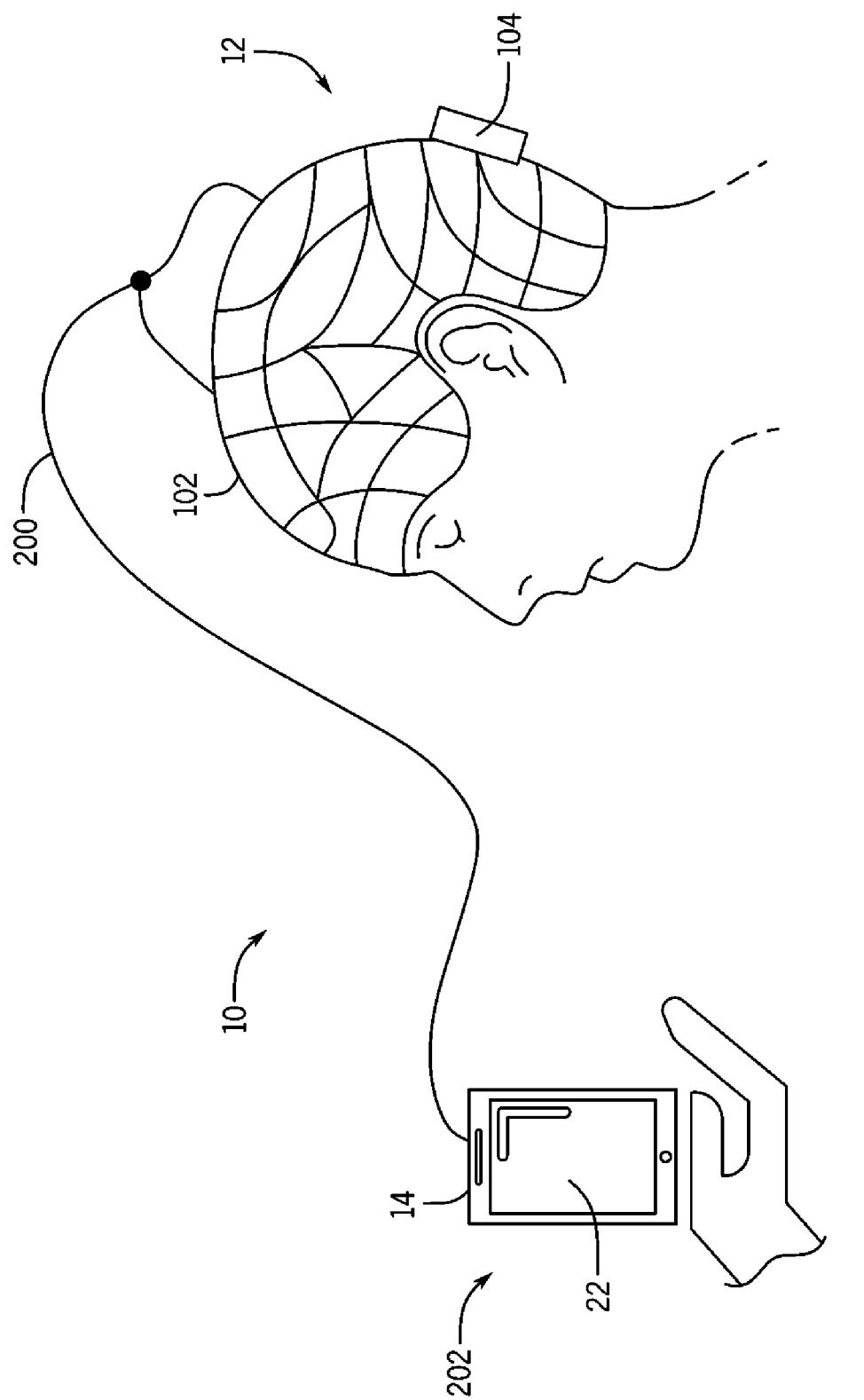
FIG. 3 is a schematic diagram of a system, in accordance with the present disclosure.

FIG. 3 is a schematic illustration of the system of FIG. 2A shows a non-limiting configuration of the system 10. Here, the system 10 includes the substrate forming the cap 102. The cap 102 may be connected via wires 200 to a computer 202, which includes the processor 14 of FIG. 1. As illustrated, the computer 202 may preferably be at least somewhat portable to facilitate field deployment of the system 10. For example, the computer 202 may be a phone or "smart phone," computer, or tablet capable of storing and running software related to the system 10. The computer may also have the output 22 integrated therewith, such as via a display, or other user interface, including printers, speakers for audible signals, or the like. To this end, the output 22, if a display, such as illustrated, may be used to facilitate the user performing a task, such as an n-back task, during at least a portion of data acquisition, such as will be described below. The computer system 202 may include an integrated power source, such as a battery, which may likewise power the cap 102 and the sensors integrated therewith. Additionally or alternatively, the cap 102 may include a power source 204, such as a battery or other power source, including wired power connections.

Figure 4:
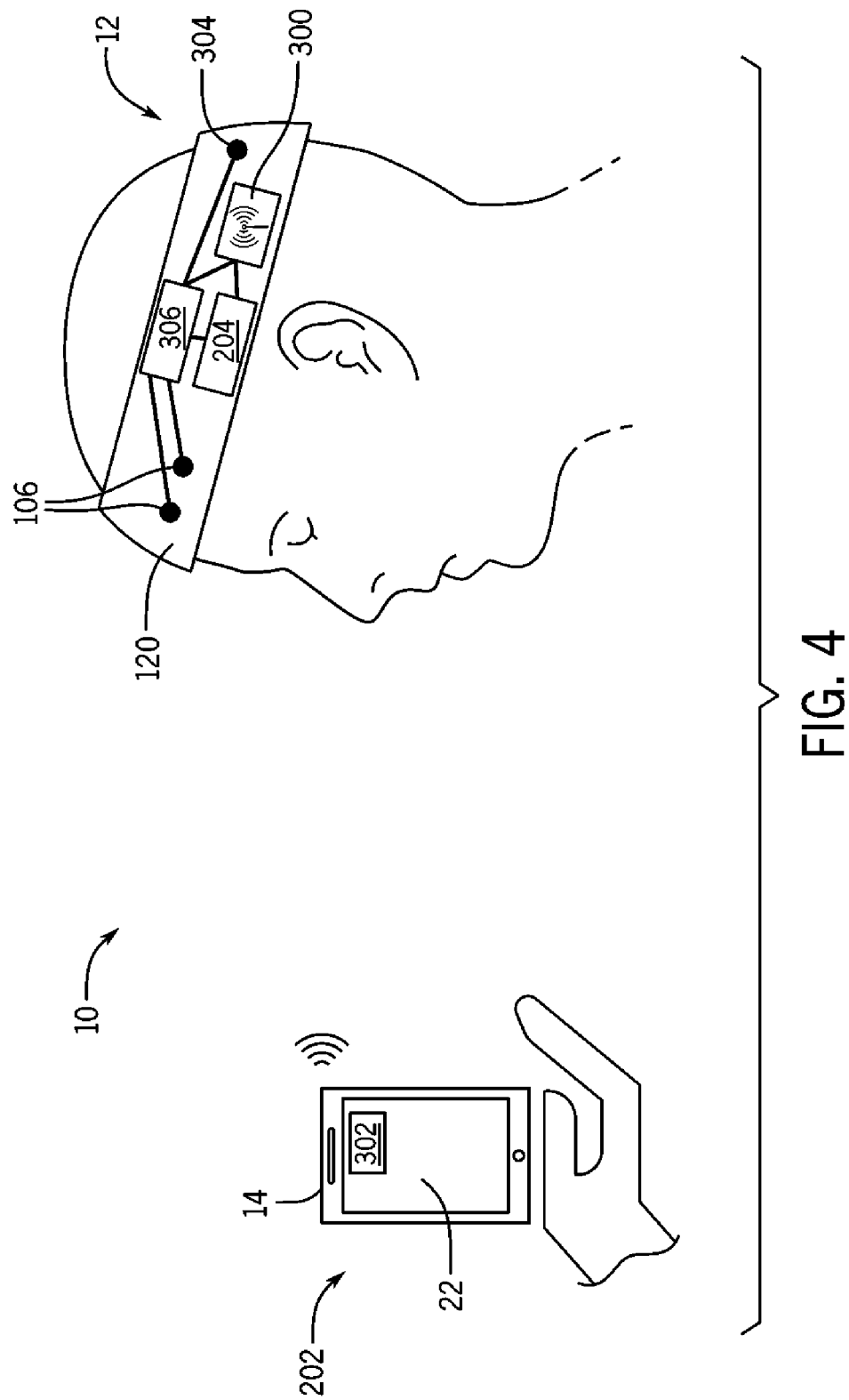
FIG. 4 is a schematic diagram of a wireless detection system, in accordance with the present disclosure.

Referring to FIG. 4, a schematic illustration of the system of FIG. 2C shows another non-limiting configuration of the system 10. In this configuration, the system 10 includes the substrate forming the headband 120. In this illustrated configuration, the headband includes an integrated wireless communication module 300 that is configured to communicate with the computer 202, which includes a respective wireless communication module 302. The headband 120 can be used to ensure that the sensors 106 are aligned and properly positioned on a subject. That is, the sensors 106 may be arranged on a side of the headband 120 that is positioned against the subject's head and aligns to be position on a particular portion of the individual, such as the subject's forehead. As one non-limiting example, the sensors 106 may be positioned so as to accurately collect data from a prefrontal cortical brain region of the individual. As will be further described, additional sensors 304 may optionally be included, for example, to acquire reference data. The sensors 106 (and optional sensors 304) may be coupled to a processor 306, which is powered by the power source 204, which likewise drives the wireless communication module 300. In this way, the sensor system 12 is capable of collecting data from the subject and communicating the data to the processor 14 in the computer 202 for analysis and communication to a user.

Figure 5:
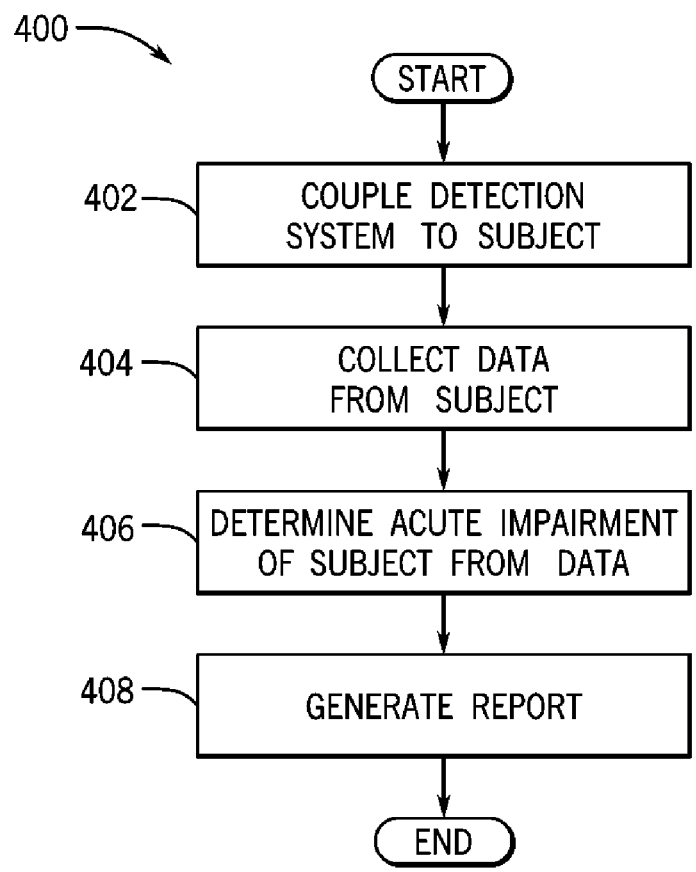
FIG. 5 is a flowchart setting forth some example steps for a method of assessing acute brain function impairment in accordance with the present disclosure.

Referring to FIG. 5, a flow chart is provided setting forth some non-limiting steps of a process 400 for using the above-described system to analyze acute brain function impairment. The process 400 begins at step 402 by coupling the detection system, such as described above, to the subject. At step 404, data is collected from the subject via the detection system.

The collected data may be biological measurement data, as will be further described. As discussed above, the detection system may perform but is not limited to performing, functional near-infrared spectroscopy (fNIRS) or electroencephalogram (EEG) analysis. In some configurations, data collection at step 404 may include only collecting one data set for the subject.

In other situations, collecting data at step 404 may include the acquisition of multiple data sets. For example, one may collect both an analysis data set, for example using the analysis sensors 106 illustrated in FIG. 4, and a reference data set, for example using the reference sensors 304 illustrated in FIG. 4. In situations where multiple data sets are to be acquired, there may be a delay period between each data set. As one non-limiting example, one data set may be obtained from the individual when impairment is suspected, and a second data set may be obtained when the individual is known to be non-impaired. Additionally or alternatively, by acquiring the reference data set from a sensor or sensors 304 that are displaced from the prefrontal cortex of the subject, the delay between acquiring the analysis and reference data sets may be reduced or eliminated. In other cases, the reference data set may not be acquired from the subject and, instead, an a priori or non-individualized reference data set may be utilized. In any case, by comparing the analysis and reference data sets, a determination of acute brain function impairment may be made.

In particular, at step 406, data is processed to determine a level of acute brain function impairment of the subject. For example, the amount of increased connectivity may be correlated to general indicators (e.g., mild, moderate, or severe brain function impairment) or may be correlated to a metric or quantitative measure of brain function impairment. In either case, the processes, as will be described, may provide an indication of the level of acute brain function impairment. For example, in situations where one, analysis, data set is acquired, the analysis data set may be compared and analyzed in view of known results that generally indicate impairment. By comparing an analysis data set for the subject to a general trend or baseline/reference data, an assessment of acute brain function impairment may be made. In some situations, the analysis data set may be normalized with other forms of data, including the reference data set. In some situations, it may be desirable to correlate impairment determinations with a secondary test. The secondary test may include, but is not limited to, breath, urine, and/or blood analysis. These processes for determining acute brain function impairment of the subject from the data at process 406 will be described in further detail with respect to some non-limiting examples. In any case, regardless of the number of data sets or the particular process utilized for analyzing the data, the process of determining an acute brain function impairment of the subject may include determining an amount of connectivity between portions of the brain of the subject and then a comparison of the amount of connectivity between portions of the brain of the subject to a reference amount of connectivity.

Finally, at step 408, a user's impairment state is communicated via a report. The report may be a displayed or written report that provides indications of a relative impairment and/or may include audio or visual communications indicating a discrete state of impairment, such as impaired or not impaired.

Figure 6:
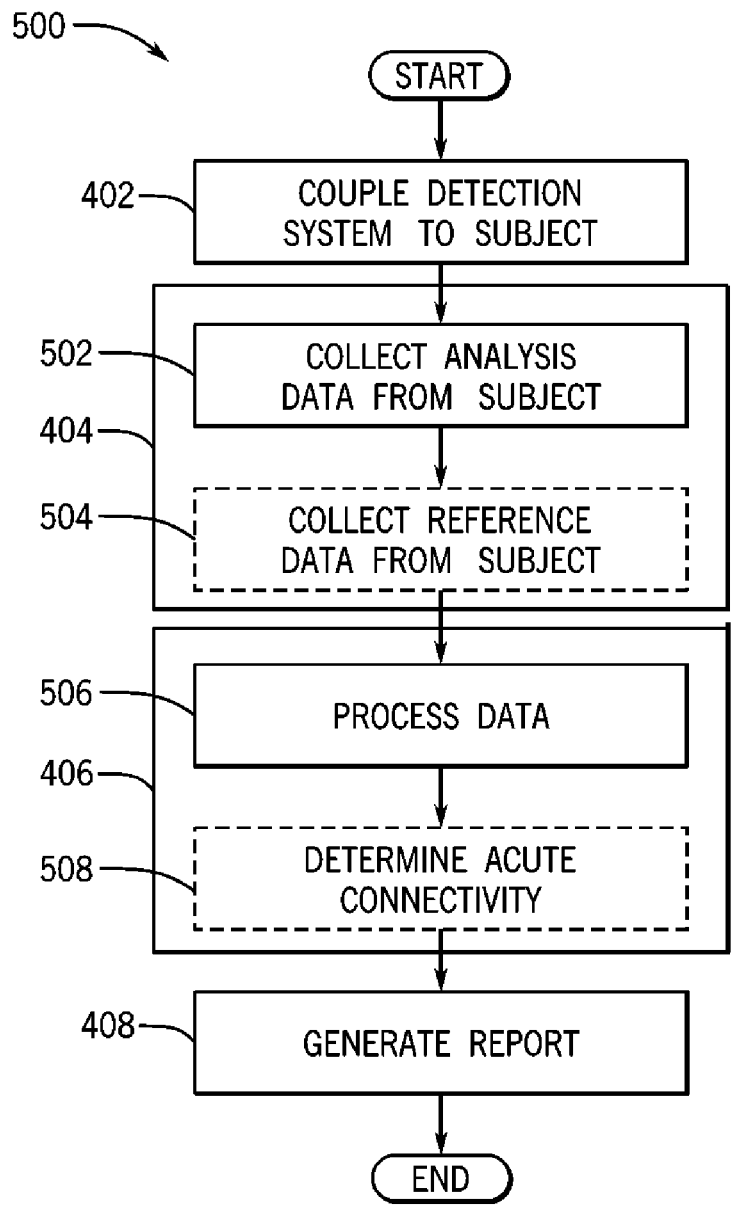
FIG. 6 is a flowchart setting forth some additional example steps for a method of assessing acute brain function impairment in accordance with the present disclosure

Referring to FIG. 6, one implementation of the process 500 described with respect to FIG. 5 may include particular data processing and analysis steps. For example, the process 500 may begin, at step 402, with coupling the detection system to the subject and conclude at step 408 with generating the above-described report or reports such as detailed below. However, in this non-limiting example, steps 404 and 406 may include a variety of sub-steps.

For example, at step 502, the detection system is used to collect analysis data from the subject. For example, the data may be neuroimaging data, such as will be described and may be acquired during the subject performing a task and at a resting state. In this way, the acquired data may be indicative of activation of the brain, from which activity or activation one can determine connectivity between regions of the brain. Also, reference data may optionally be collected from the subject at step 504. This reference data may be used, as will be described, to compare or, more specifically, normalize the analysis data.

At step 506, the acquired data may be processed to achieve a verity of outcomes. For example, the data may be processed to remove artifacts, such as can be caused by physiological functions, like cardiovascular cycles. As another non-limiting example, the data may be processed to create a correlation map or matrix and/or connectivity/correlation change matrix or map. That is, the present disclosure recognizes that impairing substances, such as THC or others, cause a subject's brain to reflect an increase in functional connectivity or correlation when the subject is impaired. Thus, at step 506, the data can be processed to determine functional connectivity or correlation of the subject, such as by creating a map or matrix of functional connectivity or correlation. If a reference data set is acquired at step 504 or is otherwise available, the map or matrix of functional connectivity or correlation created from the analysis data acquired at step 502 can be processed against the reference data, such as by performing a subtraction or other function to create a map or matrix of change functional connectivity or correlation. The reference data set can be acquired from the individual, as described, or may be assembled from a collection or database of other users.

At step 508 this processed data can optionally be fed into a trained machine learning algorithm or other resource to perform data analysis to determine further information about acute connectivity from the processed data. In this case, as will be further exemplified with respect to non-limiting Example 2 below, key information about acute impairment of the subject can be delivered, for example, by way of the reported generated at process block 408. For example, as will be described, connectivity or correlation analysis can be used to determine whether the subject is impaired or not impaired. In particular, as described in non-limiting Example 2, connectivity of brain regions on the prefrontal cortex can be used to distinguish between impaired and not impaired states. Additionally, machine learning analyses can be used to distinguish between impaired and not impaired states. Furthermore, machine learning analyses can be used to predict THC dose. Thus, the systems and methods provided herein can be used to generate diverse and insightful reports or other communications indicating acute impairment of a subject, as will be further described in the following non-limiting examples.

EXAMPLES

The present invention has been described in terms of one or more aspects, and it should be appreciated that many equivalents, alternatives, variations, and modifications, aside from those expressly stated, are possible and within the scope of the invention.

Reference is now made to the following examples, which together with the above descriptions illustrate the invention in a non-limiting fashion.

Example 1

In one study, 17 healthy, adult, weekly or greater MJ users, aged 18-55 participated the study. Experienced MJ users were selected because they are a population that is more likely to drive while intoxicated. During their first visit, participants provided detailed information on their health and drug use habits, provided a urine sample for qualitative detection of opiates, cocaine, and amphetamines and quantitative detection of (−)-11-nor-D9-THC-carboxylic acid (THC-COOH), the primary metabolite of THC. Participants were required to test positive for cannabis, and negative for all other illicit drugs at the screening visit to participate.

Participants were given MARINOL® (dronabinol), an FDA-approved synthetic form of cannabis that is used to treat loss of appetite that causes weight loss in people with AIDS. Dronabinol contains synthetic THC, the principle psychoactive drug in MJ. Participants received 5-50 mg of THC, based on the recommendation of a study physician, who assessed factors such as height, weight, age, gender, MJ use patterns (to estimate tolerance to the effects of THC), and general health of the participant. Using systems with capabilities such as described above, two sets of fNIRS data were acquired from each subject. The first set of data was acquired before the THC administration and formed a reference data set such as described above. The second set of data was acquired approximately 90 minutes after the dose of THC was administered, when peak effects were reported. Participants had blood pressure and heart rate measurements at 15-minute intervals throughout the study.

fNIRS Acquisition and Analysis

Acquisition of Neuroimaging Data:

Functional data was collected using a continuous-wave NIRSport device (NIRx Medical Technology, New York). Data was collected with a sampling frequency of 7.8 Hz, using two wavelengths of light (760 nm and 850 nm), from 8 sources, using 8 detectors (3 cm long source-detector separation) located on the forehead, following the international 10-20 system to cover prefrontal brain regions. This source-detector geometry resulted in data acquired from 20 channels. Before recording, automated calibration of the optimum gain, or signal amplification, was determined by NIRstar (V 14-1, NIRx Medical Technology, New York). This automatic calibration provided a desirable signal to noise ratio (SNR), based on the signal's coefficient or variation, for each source-detector. Following NIRS acquisition, the source and detector locations were obtained using a 3D digitizer (Polhemus Inc., VT). For task control markers, presentation software (Neurobehavioral Systems Inc.) sent trigger signals to the NIRSport device.

fNIRS Tasks:

Each fNIRS session included a 6-minute resting state scan and an approximately 6-minute n-back task. These sessions were done both before and after THC administration, as described above. The n-back task is one of the most widely used tasks to measure working memory. In this task, participants are presented with a stream of stimuli, and must decide for each stimulus whether it matches the one presented 'N' items before. Studies consistently find that N-back performance is associated with activation in prefrontal regions, and has been used often in fNIRS studies because of its ability to activate the PFC. In this study's task, participants were presented with 6 blocks; each block included 30 seconds of 2-back performance, interspersed with 20 seconds of 0-back performance (an attentional control).

fNIRS Data Analysis:

Intensity signals acquired using the fNIRS sensors were converted into optical density (OD) signals for each source-detector pair. The signal was inspected for the effects of motion and other artifacts. Motion artifacts (identified as signal variations >5% of the standard deviation of the signal within a time-period of 1 second) were detected and removed using Homer2, based on Matlab (Mathworks. Natick, MA), using removal approaches such as a channel-based cubic spline interpolation or Wavelet filtering. fNIRS signals were preprocessed by bandpass filtering (0.01-0.5 Hz) in order to reduce slow drifts and physiological noise (e.g., heart rate). Hemoglobin (Hb) concentration changes were computed by the Modified Beer-Lambert law. fNIRS Power Spectral Density (PSD) from all channels were computed. The fNIRS PSDs typically have a peak at 0.1 Hz (Mayer waves), which is especially pronounced for oxygenated Hb (HbO). The General Linear Model with systemic regressors approach was used for estimating the hemodynamic response function (HRF) to cognitive tasks and at rest, before and after THC and placebo for each channel of each participant. The response was modeled using Gaussian function. The virtual registration approach was used to register fNIRS data to MNI standard brain space. Cortical areas covered by each channel were identified with methods developed by Tsuzuki and Singh by using MNI atlas. This method allowed for placement of a virtual probe holder on the scalp by simulating the holder's deformation and by registering probes and channels onto reference brains in our MRI database. For data reduction purposes, a region of interest (ROI) approach may be used, in which the HRFs, obtained by GLM analysis for each condition and each channel, were averaged across channels over 5 ROIs encompassing 5 general PFC regions: rightmost, right of center, center, left of center, and leftmost. The primary metric of interest for each ROI was mean change in HbO between baseline and 30 sec.

Resting State Analyses:

NIRS detector data for each channel was converted to the time-dependent concentrations of HbO and HbR according to the Beer-Lambert law. Resting state data was band-pass filtered between 0.009 and 0.08 Hz, removing possible physiological noise (e.g., heart beat (~0.8 Hz), cardiac cycles (~1 Hz). Principal Component Analysis was applied to reduce the effect of systemic physiology (hearth rate, blood pressure and respiration). Motion detection and removal algorithm (a spline interpolation) was applied for each channel of each participant. Correlations of signals from 20 recording channels were computed in order to measure coupling across channel pairs. The correlation matrix (20×20) was generated for each participant in PRE and POST-conditions for THC and placebo sessions. The connectivity of channels were represented by an undirected binary adjacency matrix. The binary matrices were generated by applying a threshold to the correlation matrix.

Machine Learning Analysis

Resting StateNascular Connectivity Data:

In the classification analysis for resting state data, the subject-level change in fNIRS connectivity was first computed by subtracting the pre-THC connectivity matrix entries from the post-THC fNIRS connectivity matrix. The connectivity change matrix was then used as input to a Support Vector Machine regression (SVM-R) model or to a random forest machine learning model. Four outcomes were to be predicted: (1) THC dose, (2) THC vs. Placebo state, (3) Impairment Status (Impaired vs Not Impaired), and (4) subjective intoxication response, The Matlab implementation of SVM-R, called fitrsvm, was used. A leave-1-out cross-validation was conducted, where, at each iteration, one subject was left-out as a test case, and all remaining subjects served as the impairment data that was used to train SVM-R given their ground truth data. Then, using the trained model, outcomes were predicted on each test case and was compared with the ground truth value for that case. This iteration was repeated for all subjects. The effect of training data size on prediction accuracy was analyzed. Finally, a power-law model was fit to the prediction performance (correlation) versus sample size curve. All analyses were performed using the R statistical programming language.

N-Back Cognitive Data:

For the n-back cognitive data, a standard stepwise linear discriminant analysis algorithm was applied to the fNIRS data with the goal of discriminating between the THC and no-THC condition, and a leave-one-out cross validation (on 17 subjects) as described above, and a 50% classification threshold was used. These analyses used all 20 channels with a common average spatial filter. After averaging, the algorithm selected the channels with the largest difference between pre- and post-THC conditions.

Results

Figure 7:
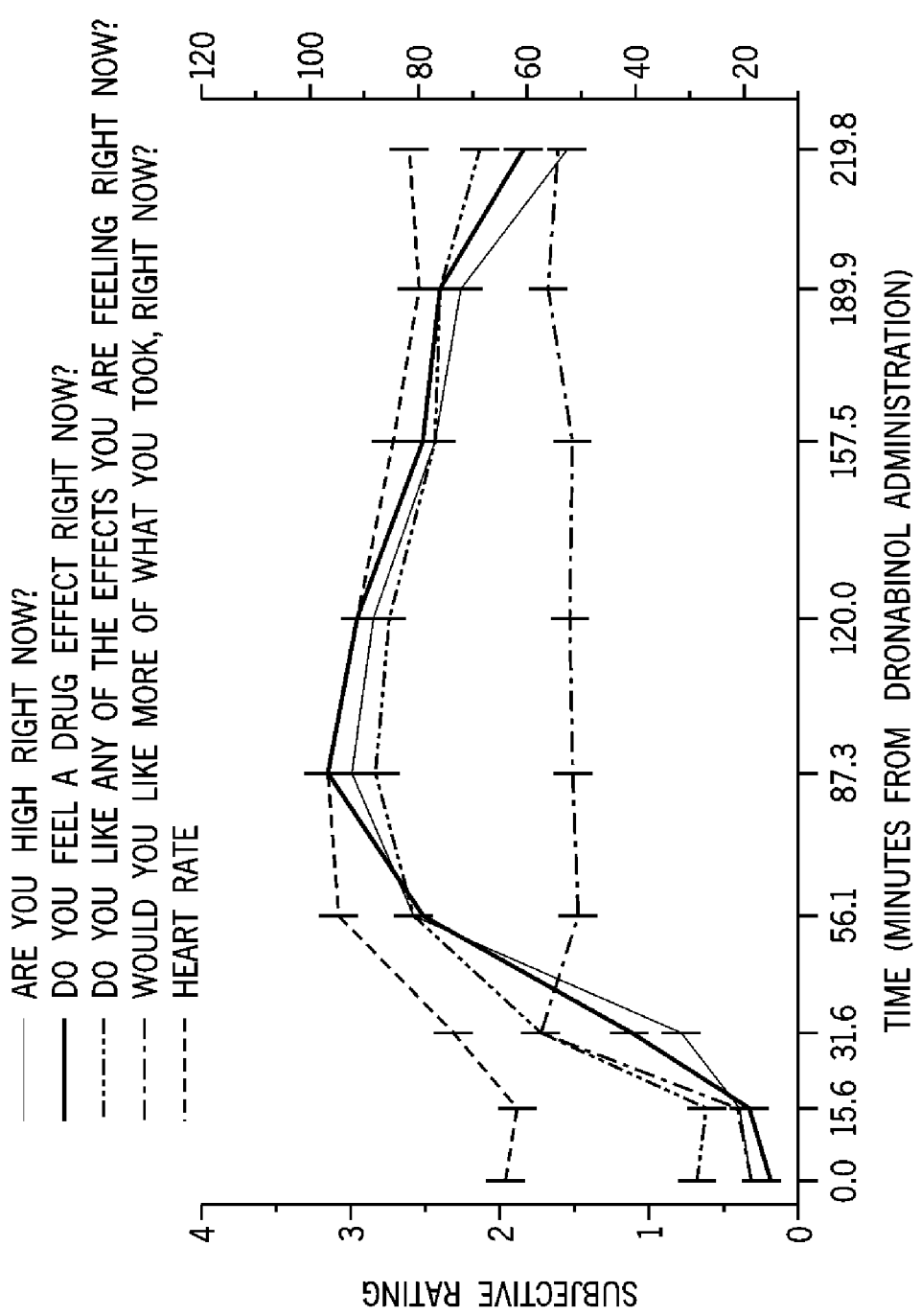
FIG. 7 is a graph showing experimental data relating to heart rate and self-reported intoxication, in accordance with the present disclosure.
Figure 8:
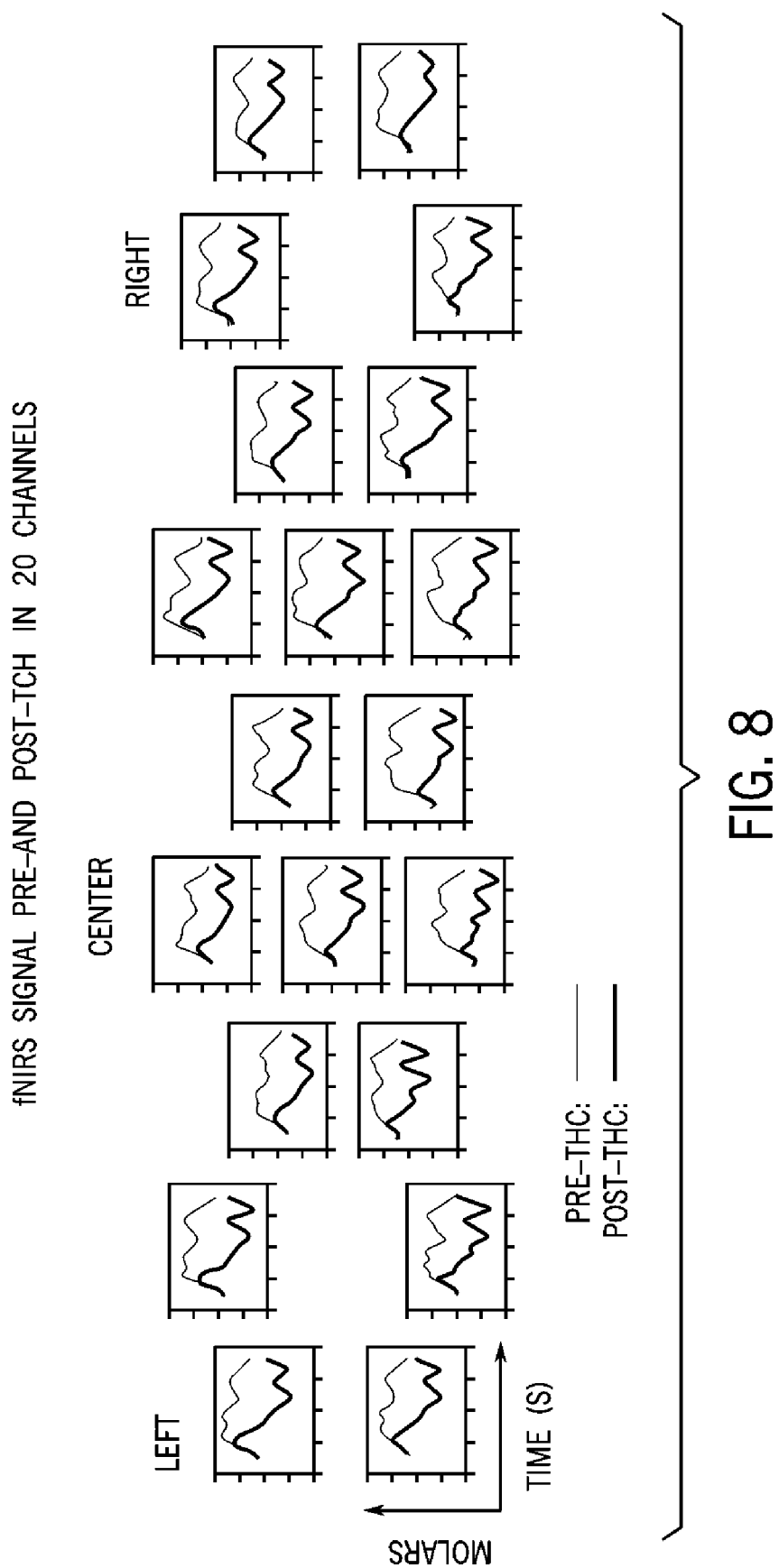
FIG. 8 is a series of graphs showing experimental data of pre- and post-THC dosing block averages, in accordance with the present disclosure.

THC Produced Expected Physiological/Psychological Effects:

As shown in FIG. 7, heart rate increased approximately 30 bpm after THC dosing and preceded peak subjective high as assessed with the DEQ. Subjective high peaked 90 minutes after THC administration.

fNIRS Signal Distinguished Pre- Vs Post-THC Brain Signals:

fNIRS data was block-averaged to obtain the hemodynamic response function (HRF) during activation blocks of the N-back task. Motion artifacts were identified using the automated Homer2 process and corrected using channel-based cubic interpolation. Baseline was set to zero by subtraction of the average signal for t<0. Graphing of pre- and post-THC block averages revealed robust signal differences by drug condition, as illustrated in FIG. 8. The first component in a Principal Components analysis, a linear combination of all channels, revealed a large difference between pre and post THC fNIRS signal, p=0.0058.

Figure 9A:
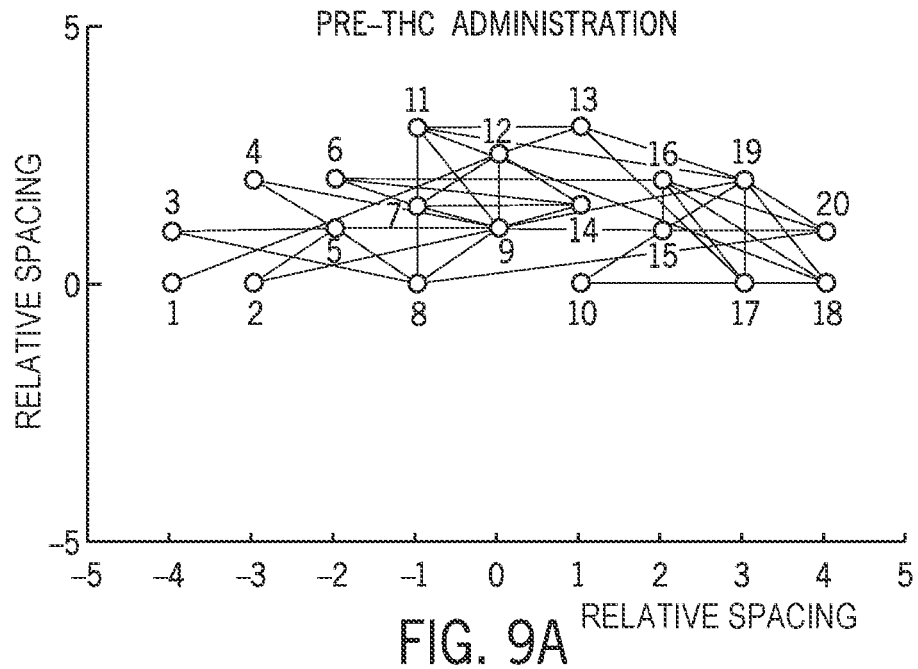
FIG. 9A is a graph showing experimental data of prefrontal cortical functional connectivity pre-THC dosing, in accordance with the present disclosure.
Figure 9B:
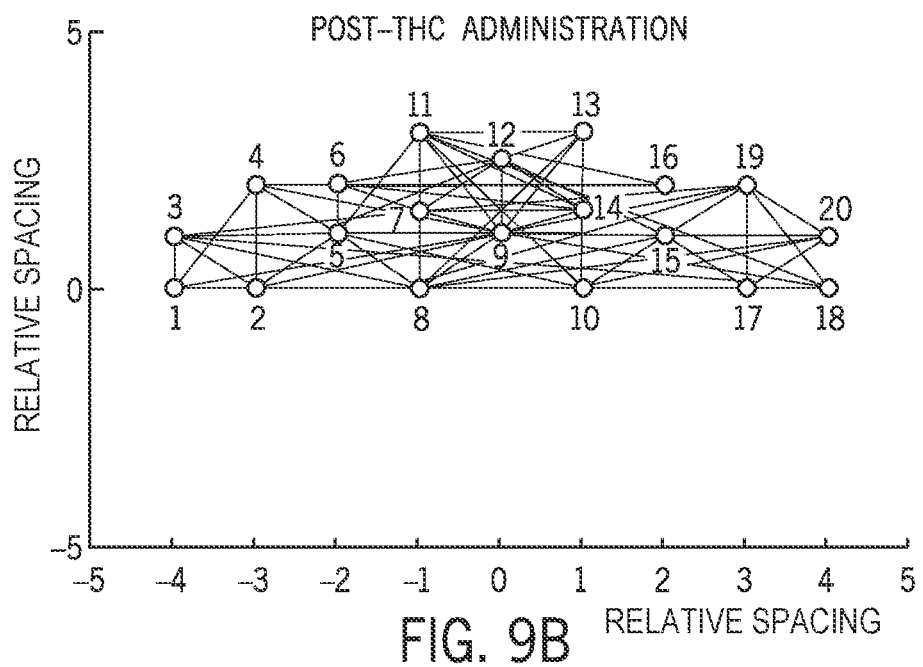
FIG. 9B is a graph showing experimental data of prefrontal cortical functional connectivity post-THC dosing, in accordance with the present disclosure.

Classification Accuracy:

Prefrontal cortical functional connectivity at rest (RSFC) (e.g., not during performance of a cognitive task) was increased after THC dose, as shown in FIGS. 9A and 9B. For these analyses, a connectivity matrix was generated for each subject according to the following steps:

(1) NIRS detector data for each channel was converted to the time-dependent concentrations of HbO and HbR.

(2) Correlations of signals from 20 recording channels were computed in order to measure coupling across channel pairs.
(3) The correlation matrix (20×20) was generated for each participant in PRE and POST-conditions for THC and placebo sessions.
(4) The connectivity of channels were represented by an undirected binary adjacency matrix. The binary matrices were generated by applying a threshold to the correlation matrix.
(5) The connectivity for each channel pair was determined by the Pearson linear correlation coefficient (Pearson's r), averaged among all subjects for both THC and placebo trials.
(6) A connectivity change matrix of pre-THC connectivity entries subtracted from the post-THC fNIRS connectivity matrix was used as input to a Support Vector Machine regression (SVM-R) model.

In this example implementation, this model predicted THC dose as the continuous outcome of interest (n=17, 5-50 mg THC, mean 32.6 mg, std 15.2 mg) using Matlab implementation of SVM-R, fitrsvm. Using leave-1-out cross-validation, where, at each iteration, one subject was left-out as a test case, and remaining (N−1=16) subjects were used to train SVM-R given their ground truth data, dose was predicted on each test case. SVM-R achieved a prediction accuracy with a root mean squared error (RMSE) of 11.4 mg, (R=0.66, P=0.0035).

Figure 10A:
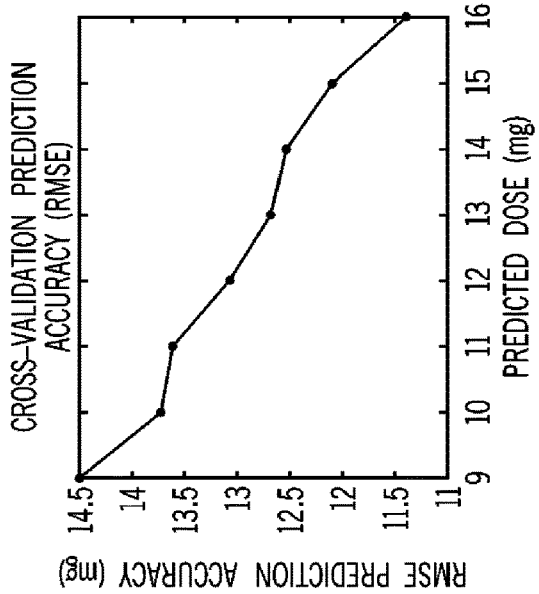
FIG. 10A is a graph showing experimental data of predicted vs ground truth dose data, in accordance with the present disclosure.
Figure 10C:
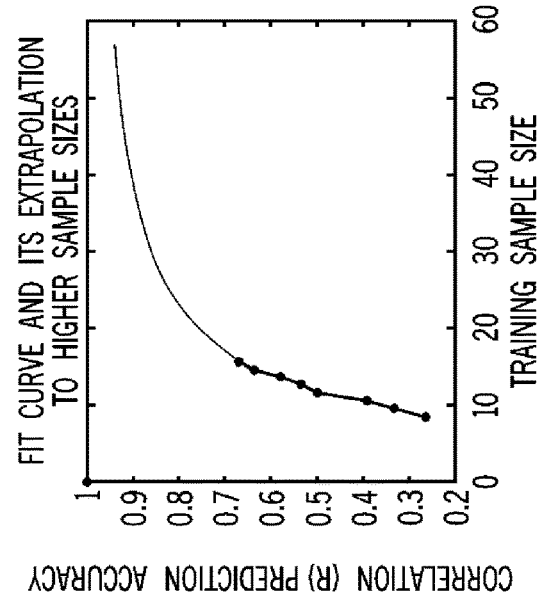
FIG. 10C is a graph showing experimental cross-validation prediction accuracy as a function of training sample size, in accordance with the present disclosure.
Figure 10B:
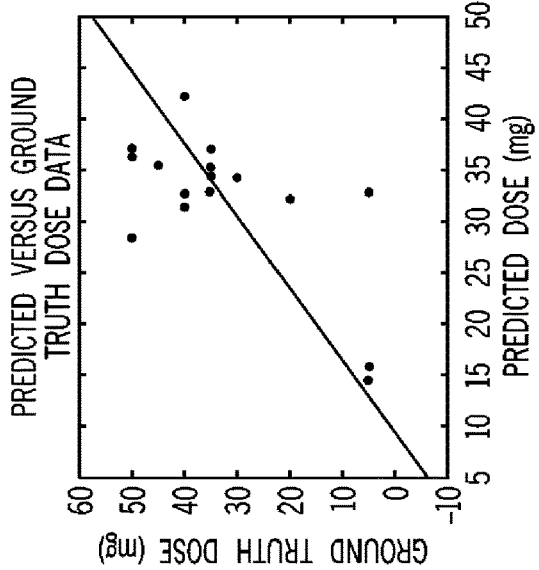
FIG. 10B is a graph showing experimental cross-validation prediction accuracy as a function of training sample size, in accordance with the present disclosure.
Figure 10D:
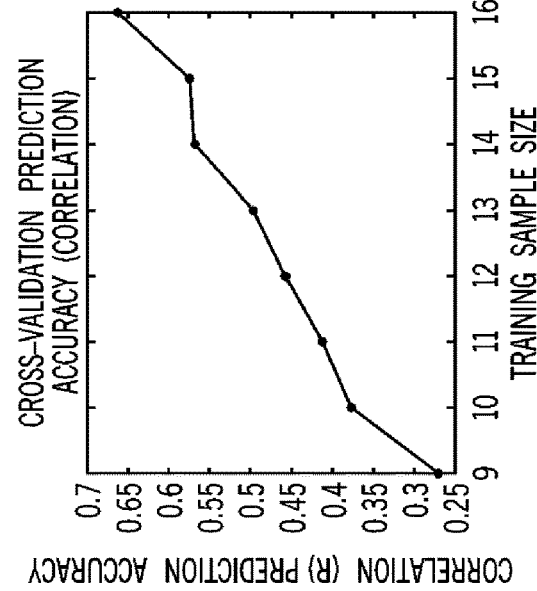
FIG. 10D is a graph showing an experimental fit curve and its extrapolation to larger sample sizes, in accordance with the present disclosure.

FIG. 10A illustrates the predicted versus ground truth dose data. In order to evaluate the sample size needed for prediction accuracy of at least 90%, the effect of training data sample size on prediction accuracy was analyzed. A leave-k-out cross-validation was used, where k was varied from 2 through 8. At k=8, for example, only about half of the total sample (N=9) was used for training, whereas at each iteration 8 subjects were left out for testing. FIGS. 10B and 10C plot cross-validation prediction accuracy (RMSE and correlation, respectively) as a function of training sample size. These results suggest that increasing the training data sample size may improve prediction performance. To further demonstrate this, a power-law model was fit to the prediction performance (correlation) versus sample size curve shown in FIG. 10C. The fit curve and its extrapolation to larger sample sizes is visualized in FIG. 10D.

N-back Cognitive Data:

A standard stepwise linear discriminant analysis algorithm was applied to the fNIRS data to discriminate between the THC and no-THC condition. With a leave-one-out cross validation (on 17 subjects) and a 50% classification threshold, using an approach in which 1 of the 2 tests for each subject is known to be positive for THC, THC was classified from no-THC with an accuracy of 82.35%. These analyses used all 20 channels with a common average spatial filter. After averaging, the algorithm used primarily channels 2 and 3 (covering the left dorsolateral prefrontal cortex (DLPFC)).

Example 2

Figure 11:
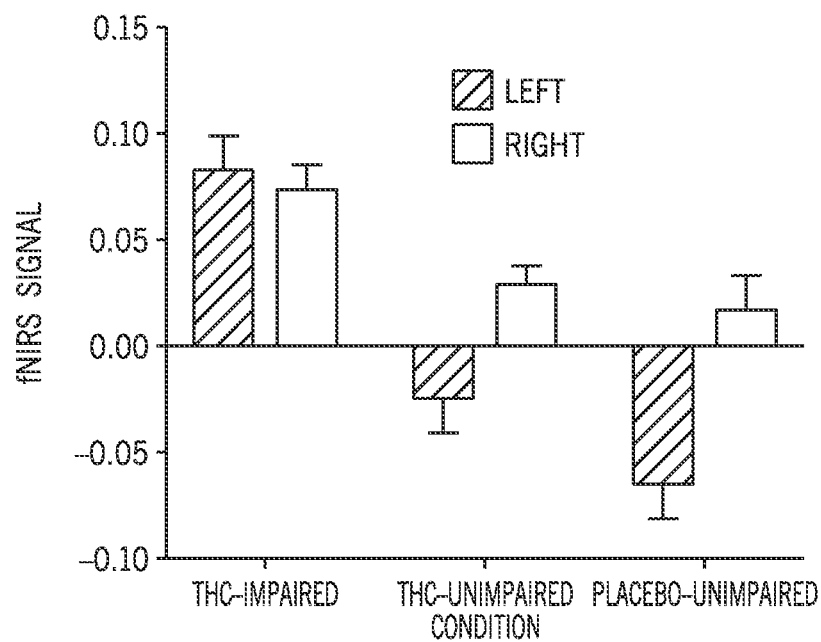
FIG. 11 is a graph showing experimental data comparing left and right prefrontal cortex activation for impaired and unimpaired individuals, in accordance with the present disclosure.
Figure 12:
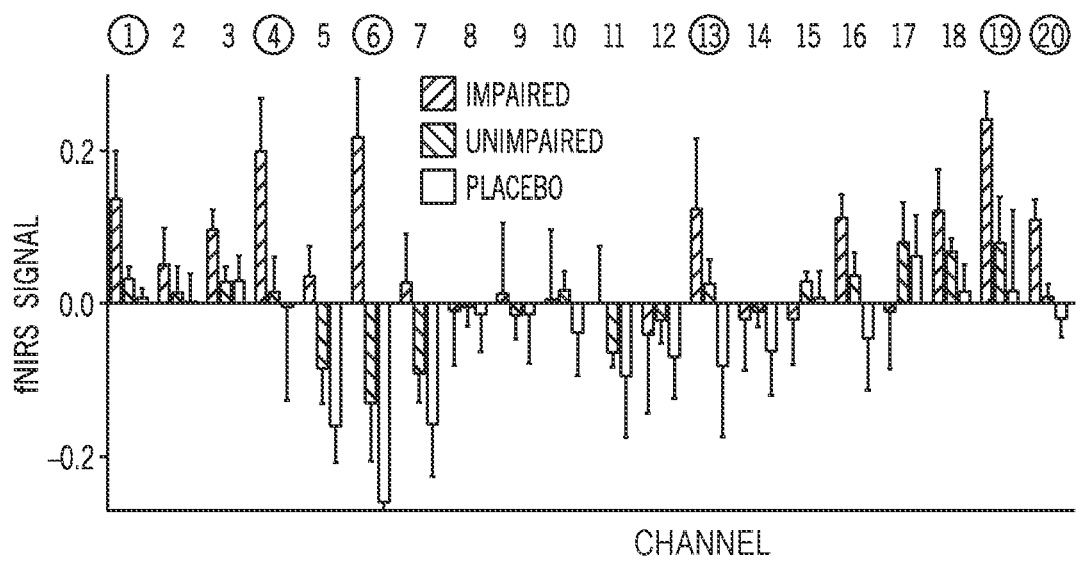
FIG. 12 is a graph showing a channel-specific analysis on the experimental data of FIG. 11, in accordance with the present disclosure.

Activity of the PFC—Impaired Vs not Impaired:

In a second study that employed a double-blind, placebo-controlled, random order dosing design, the differences between participants deemed "impaired" vs "not impaired" by the gold standard field sobriety test conducted by an expert, certified Drug Recognition Expert (DRE) were evaluated. Importantly, differences were found in activation in the left and right prefrontal cortex (PFC) (averaging among all channels left or right of midline) not only between those who received THC and were deemed impaired by a DRE vs those who received placebo, but also between those who received THC and were assessed by the DRE as impaired vs those who received THC and were assessed to be not impaired (among all participants who received THC) (FIG. 11). For example, FIG. 12 illustrates a channel specific analysis of individuals on THC and classified by DREs as impaired, on THC and classified by DREs as not impaired, and on placebo.

Figure 13:
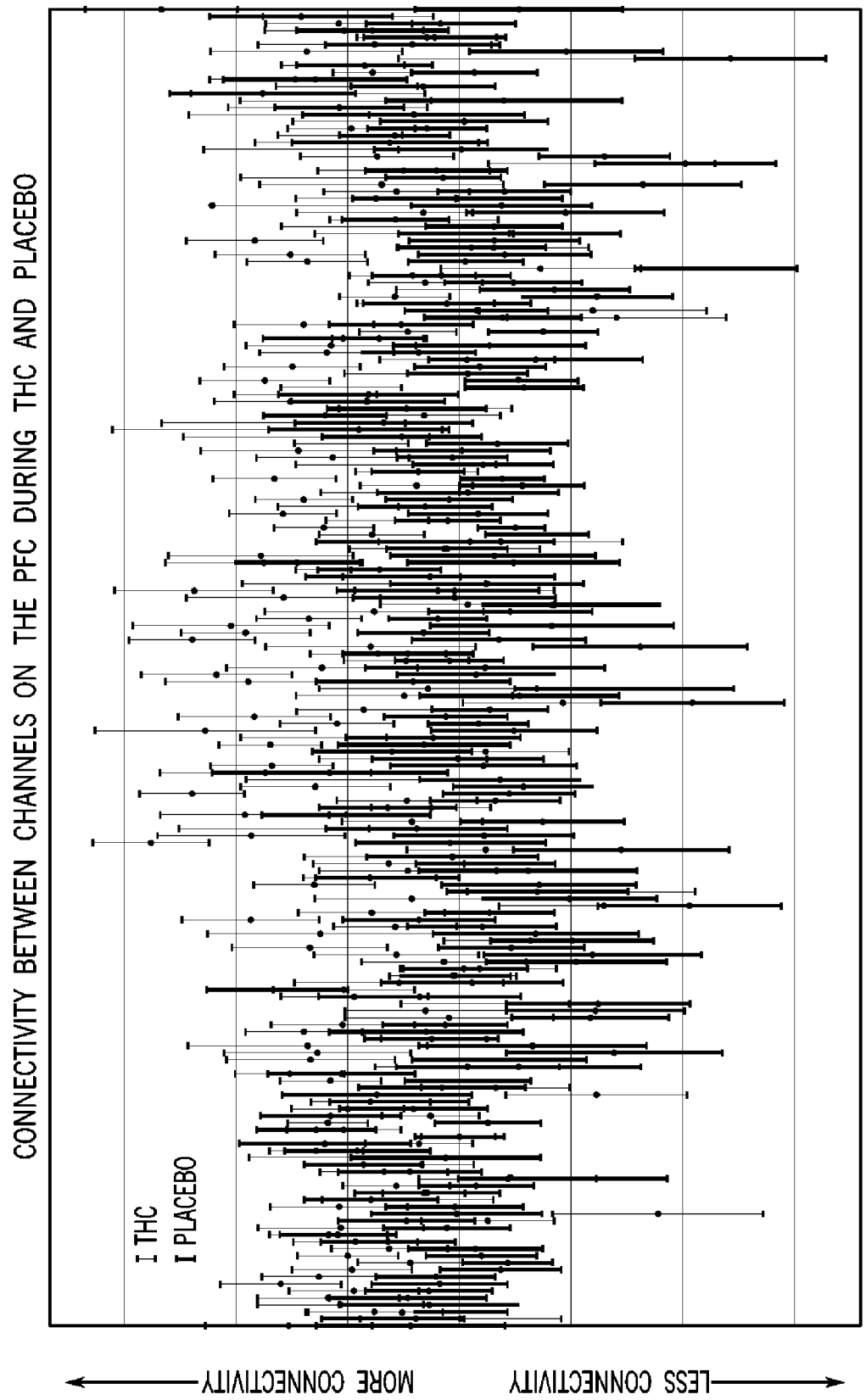
FIG. 13 is a graph of experimental connectivity between prefrontal cortical channels after THC and placebo dosing, in accordance with the present disclosure.

Connectivity of Brain Regions in the PFC can Distinguish Between THC and Placebo Administration:

The normalized connectivity data was first visualized to check for patterns and possible trends. The data was divided into two halves representing all visits where the subject received a placebo and all visits where the subject received THC. Means and standard error were computed for each channel-channel correlation and these statistics were examined using a forest-plot style visualization, as shown in FIG. 13.

Figure 14:
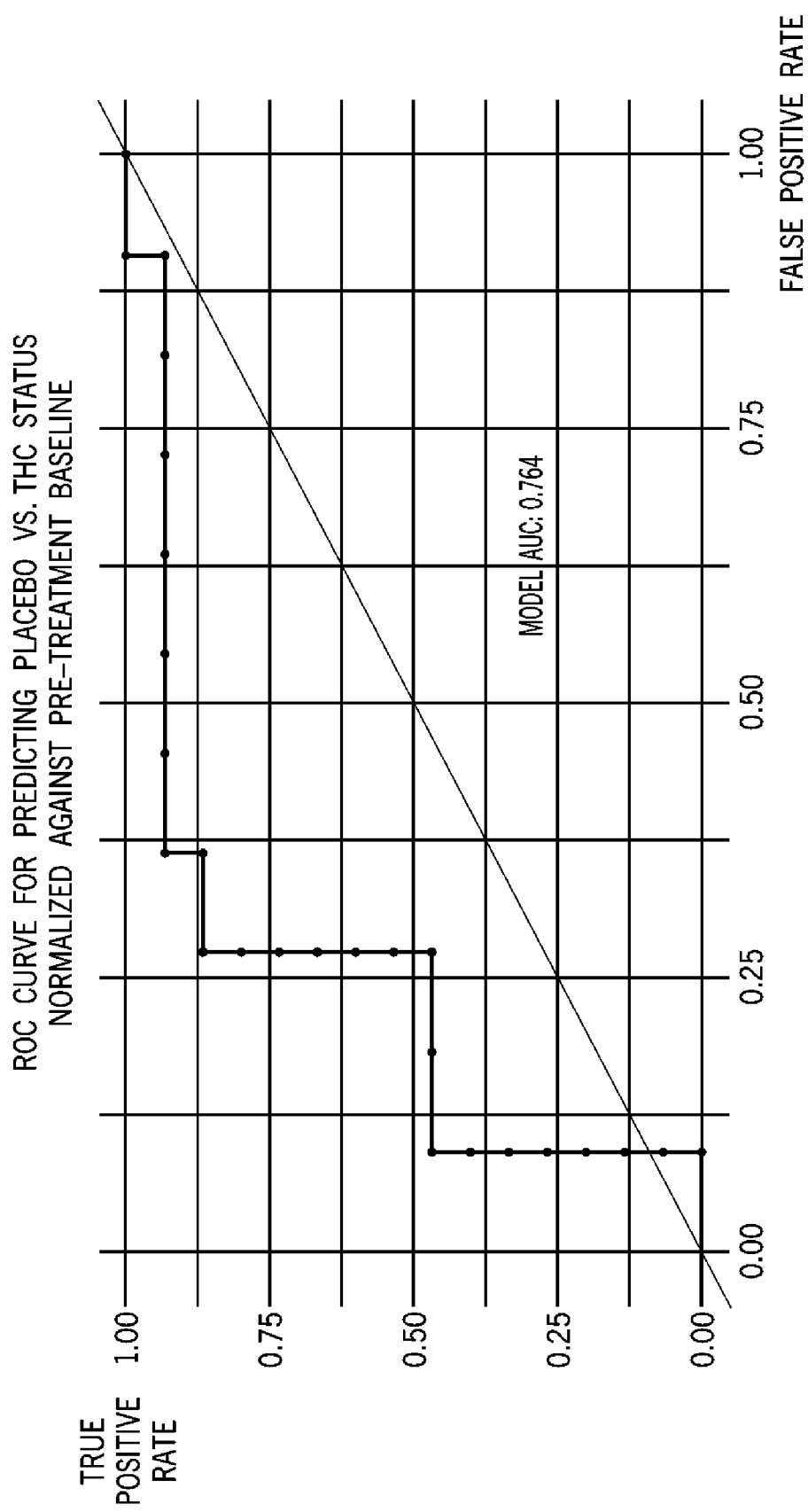
FIG. 14 is a receiver-operator characteristic (ROC) curve for a machine learning model, in accordance with the present disclosure.

Machine Learning Analyses can Distinguish Between THC and placebo:

With a leave-one-subject-out cross validation (on 25 subjects) and a 50% classification threshold, THC was classified from no-THC with an accuracy of 75.2% and an AUC of 0.764. The model was a random forest with 500 trees, which randomly selected two variables at each iteration for use in an individual tree. The receiver-operator characteristic (ROC) curve for this model is shown in FIG. 14.

Figure 15:
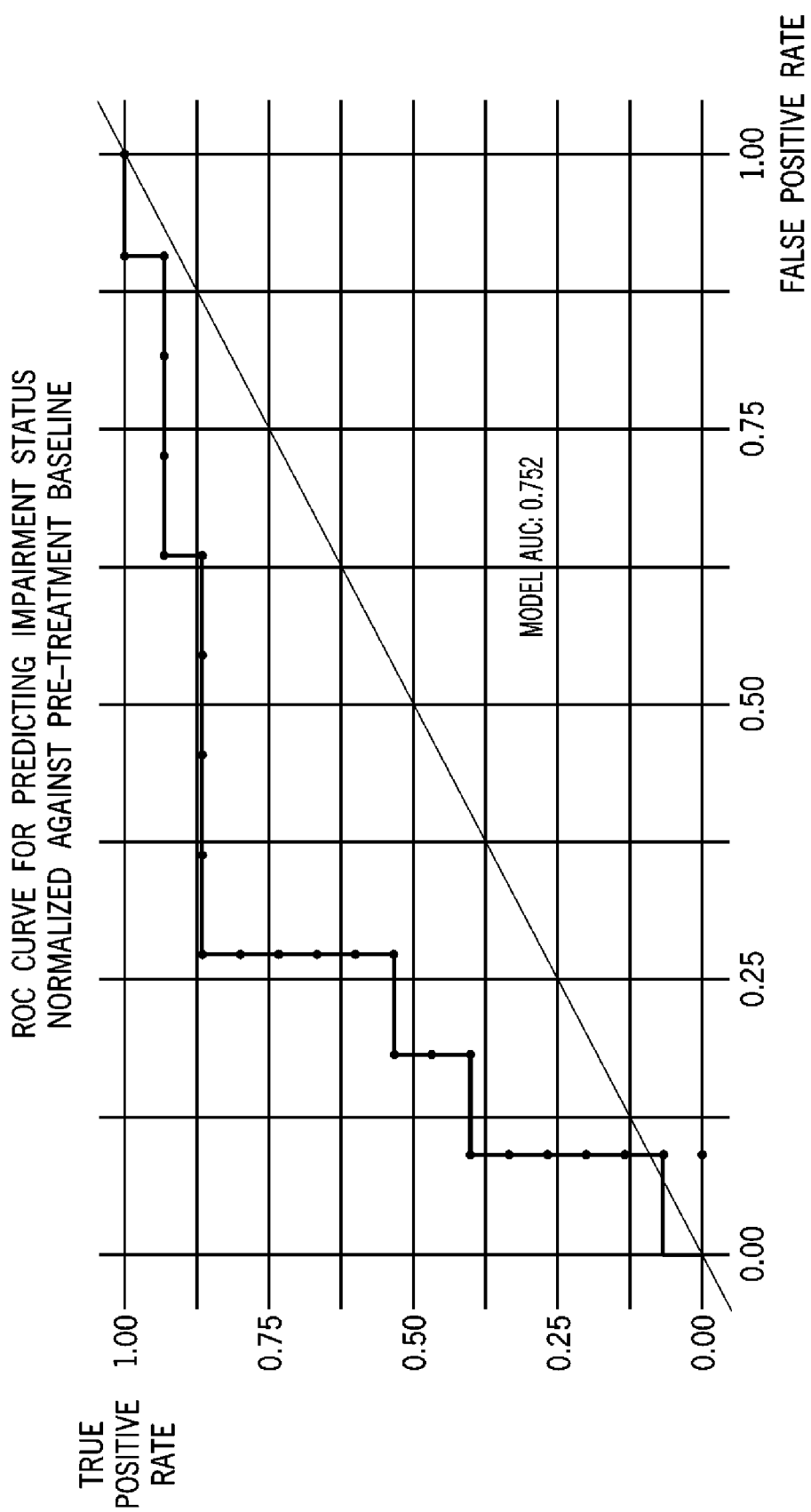
FIG. 15 is another ROC curve in accordance with the present disclosure.

Machine Learning Analyses can Distinguish Between Impaired and Not Impaired:

With a leave-one-subject-out cross validation (on 25 subjects) and a 50% classification threshold, THC was classified from no-THC with an accuracy of 65% and an AUC of 0.75. This model was identical to the random forest model described in the previous section. The ROC curve is shown in FIG. 15.

Machine Learning Analyses Showed that Self-Reported Intoxication is Inaccurate:

With a leave-one-subject-out cross validation (on 25 subjects), the DEQ score was predicted using a random forest model with 500 trees, where all variables were used at each tree-building iteration. This model had an R^2 value of 3%, indicating that machine learning techniques did not reflect self-reported intoxication. This indicates that individuals had limited insight into whether or not they were impaired.

Figure 16:
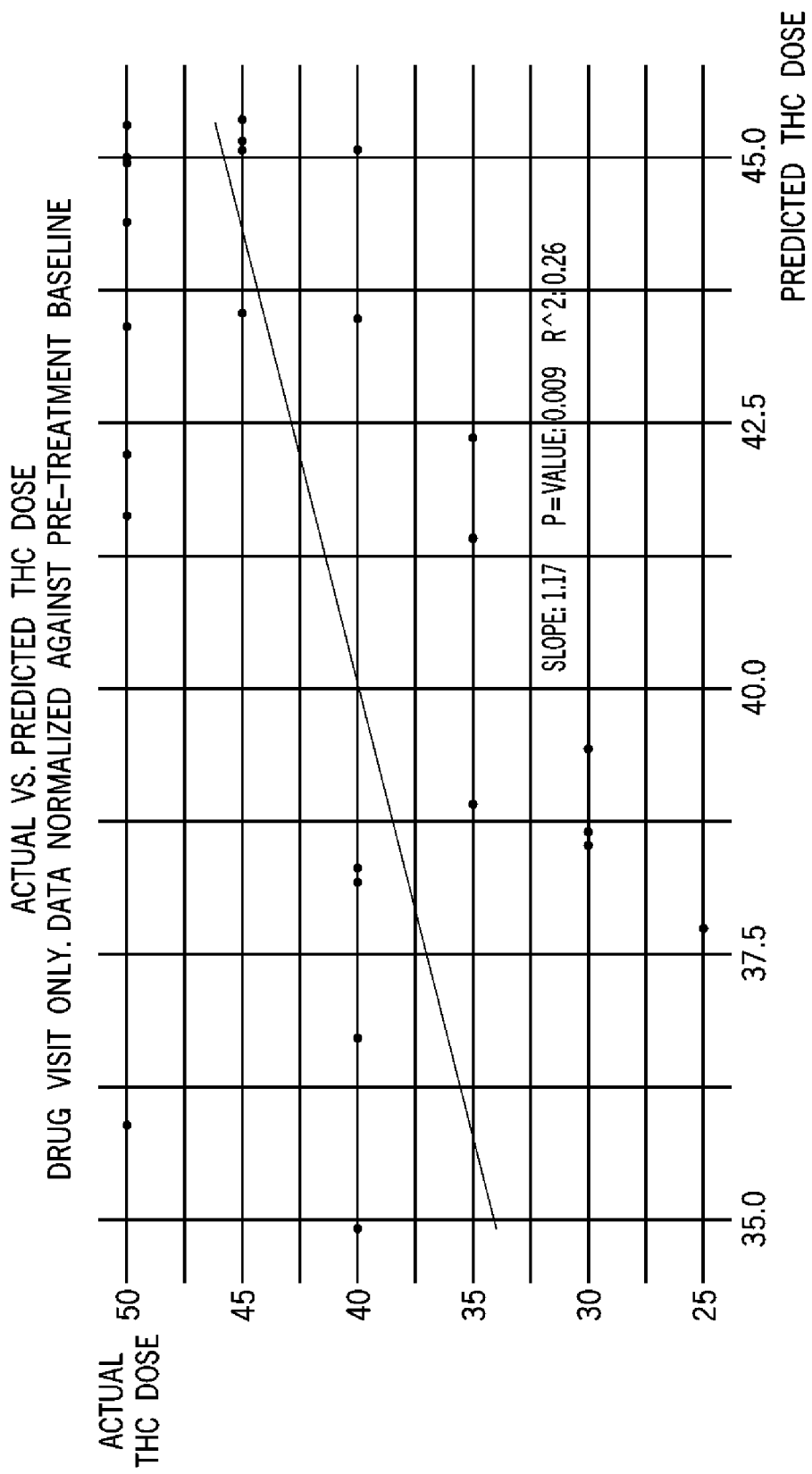
FIG. 16 is a plot of predicted vs actual values for THC dose, in accordance with the present disclosure.

Machine Learning Analyses can Predict THC Dose:

Using leave-one-subject-out cross-validation, random forest regression was performed to predict the dose of THC each subject received during their drug visit. The model had a mean squared-error 6.5 mg and an R^2 value of 0.26 and a Pearson correlation coefficient of 0.5 (p<0.001) between the actual and predicted values. A plot of the predicted vs. actual values is shown in FIG. 16.

For the avoidance of doubt, aspects of the present disclosure described with respect to the systems are applicable to the methods and aspects described with respect to the methods are applicable to the systems.

It will be appreciated by those skilled in the art that while the invention has been described above in connection with particular embodiments/aspects and examples, the invention is not necessarily so limited, and that numerous other aspects, examples, uses, modifications and departures from the aspects, examples and uses are intended to be encompassed by the claims attached hereto.

The invention claimed is:

1. A system for determining an acute brain function impairment of a subject, the system comprising:
   a sensor system configured to acquire signals indicative of a function of a brain of the subject, wherein the sensor system includes a first set of sensors configured to acquire the signals from the prefrontal cortex and a second set of sensors configured to acquire the signals from an area of the brain outside the prefrontal cortex;
   a processor configured to receive the signals from the sensor system and configured to:
      analyze the signals to determine an amount of functional connectivity between portions of the brain of the subject from the signals acquired from the first set of sensors and a reference amount of functional connectivity from the signals acquired from the second set of sensors;
      compare the amount of functional connectivity between portions of the brain of the subject to the reference amount of functional connectivity;
      determine acute physical and/or mental performance deficiencies caused by consumption of intoxicants of the subject based on the comparison of the amount of functional connectivity between portions of the brain of the subject to the reference amount of functional connectivity; and
      generate a report indicating the acute physical and/or mental performance deficiencies of the subject.

2. The system of claim 1, wherein the sensor system includes a plurality of near infrared spectroscopy (NIRS) sensors configured to acquire the signals.

3. The system of claim 2, wherein the plurality of NIRS sensors includes eight sensors configured to be arranged along a forehead of the subject.

4. The system of claim 1, further comprising a headband configured to arrange the sensor system to acquire the signals from the prefrontal cortex of the subject.

5. The system of claim 1, further comprising a display configured to display the report.

6. The system of claim 1, wherein the processor is configured to implement a machine learning architecture to perform at least one of the analyzing, comparing, and determining.

7. The system of claim 6, wherein the machine learning architecture includes a random forest architecture trained on impairment data from subjects having been administered Δ9-tetrahydrocannabinol (THC).

8. The system of claim 1, wherein the report includes a quantitative indication of the acute physical and/or mental performance deficiencies of the subject based on an increase in the amount of functional connectivity between portions of the brain of the subject compared to the reference amount of functional connectivity.

9. A method for detecting acute impairment, the method including steps comprising:
   a) acquiring, with a sensor system, signals from a subject indicative of brain functionality of the subject, including acquiring the signals from the prefrontal cortex from a first set of sensors and acquiring the signals from an area of the brain outside the prefrontal cortex from a second set of sensors;
   b) processing, using a computer processor, the signals to determine functional connectivity between portions of the brain of the subject from the signals acquired from the first set of sensors and a reference amount of functional connectivity from the signals acquired from the second set of sensors;
   c) determining, using the computer processor, whether the functional connectivity of the brain of the subject is indicative of acute physical and/or mental performance deficiencies caused by consumption of intoxicants of the subject based on the comparison of the amount of functional connectivity between portions of the brain of the subject to the reference amount of functional connectivity; and
   d) generating a report indicating the acute physical and/or mental performance deficiencies of the subject from the determining of step c).

10. The method of claim 9, wherein step c) includes utilizing a machine learning model trained to analyze metabolizing of Δ9-tetrahydrocannabinol (THC) by the subject.

11. The method of claim 10, wherein the machine learning model includes a Support Vector Machine regression (SVM-R) model.

12. The method of claim 10, wherein the machine learning model includes a random forest model.

13. The method of claim 9, wherein step b) includes determining an oxy-hemoglobin (HbO) concentration in the subject from the signals and determining the functional connectivity based on correlations between HbO concentration over time in the subject's brain.

* * * * *